US00PP26242P2

(12) United States Plant Patent
de Jong

(10) Patent No.: US PP26,242 P2
(45) Date of Patent: Dec. 15, 2015

(54) *HYPERICUM* PLANT NAMED 'KOLMIGLOW'

(50) Latin Name: *Hypericum×inodorum*
Varietal Denomination: Kolmiglow

(71) Applicant: Jan de Jong, Heelsum (NL)

(72) Inventor: Jan de Jong, Heelsum (NL)

(73) Assignees: Kolster Holding B.V., Boskoop (NL); Floribreed vof, Heelsum (NL)

( * ) Notice: Subject to any disclaimer, the term of this patent is extended or adjusted under 35 U.S.C. 154(b) by 100 days.

(21) Appl. No.: 13/999,251

(22) Filed: Jan. 31, 2014

(51) Int. Cl.
*A01H 5/02* (2006.01)

(52) U.S. Cl.
USPC ..... Plt./442

(58) Field of Classification Search
USPC ..... Plt./442
See application file for complete search history.

*Primary Examiner* — Susan McCormick Ewoldt
(74) *Attorney, Agent, or Firm* — C. A. Whealy

(57) ABSTRACT

A new and distinct cultivar of *Hypericum* plant named 'Kolmiglow', characterized by its upright and outwardly spreading plant habit; moderately vigorous growth habit; dark purple-colored developing stems; relatively small leaves that dark green in color with dark purple-colored lower surfaces; freely flowering habit; high fruit density; and glossy dark red-colored fruits.

4 Drawing Sheets

Botanical designation: *Hypericum×inodorum.*
Cultivar denomination: 'KOLMIGLOW'.

BACKGROUND OF THE INVENTION

The present invention relates to a new and distinct cultivar of *Hypericum* plant, botanically known as *Hypericum×inodorum* and hereinafter referred to by the name 'Kolmiglow'.

The new *Hypericum* plant is a product of a planned breeding program conducted by the Inventor in Heelsum, The Netherlands. The objective of the breeding program is to create new *Hypericum* plants with strong stems, dark-colored leaves, and numerous attractive fruits.

The new *Hypericum* plant originated from a cross-pollination conducted by the Inventor in 2009 in Heelsum, The Netherlands of a proprietary selection of *Hypericum×inodorum* identified as code number 8205-04, not patented, as the female, or seed parent with a proprietary selection of *Hypericum×inodorum* identified as code number 393-00, not patented, as the male, or pollen, parent. The new *Hypericum* plant was discovered and selected by the Inventor as a single flowering plant from within the progeny of the stated cross-pollination in a controlled greenhouse environment in Heelsum, The Netherlands in 2010.

Asexual reproduction of the new *Hypericum* plant by vegetative cuttings in a controlled greenhouse environment in Boskoop, The Netherlands since 2011 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Kolmiglow'. These characteristics in combination distinguish 'Kolmiglow' as a new and distinct *Hypericum* plant:

1. Upright and outwardly spreading plant habit.
2. Moderately vigorous growth habit.
3. Dark purple-colored developing stems.
4. Relatively small leaves that dark green in color with dark purple-colored lower surfaces.
5. Freely flowering habit; high fruit density.
6. Glossy dark red-colored fruits.

Plants of the new *Hypericum* differ primarily from plants of the female parent selection in the following characteristics:

1. Plants of the new *Hypericum* and the female parent selection differ in developing stem color as plants of the female parent selection have green-colored developing stems.
2. Plants of the new *Hypericum* and the female parent selection differ in fruit color as plants of the female parent selection have dark brown-colored fruits.

Plants of the new *Hypericum* differ from plants of the male parent selection in the following characteristics:

1. Plants of the new *Hypericum* and the male parent selection differ in developing stem color as plants of the male parent selection have green-colored developing stems.
2. Plants of the new *Hypericum* and the male parent selection differ in fruit shape as plants of the male parent selection have elliptic-shaped fruits.

Plants of the new *Hypericum* can also be compared to plants of the *Hypericum* 'Pinky Flair', not patented. In side-by-side comparisons, conducted in Boskoop, The Netherlands, plants of the new *Hypericum* differed primarily from plants of 'Pinky Flair' in the following characteristics:

1. Plants of the new *Hypericum* and 'Pinky Flair' differed in leaf lower surface color as plants of 'Pinky Flair' had leaves with green-colored lower surfaces.
2. Plants of the new *Hypericum* and 'Pinky Flair' differed in flower bud color as plants of 'Pinky Flair' had yellow-colored flower buds.

3. Plants of the new *Hypericum* and 'Pinky Flair' differed in fruit luster and color as plants of 'Pinky Flair' had matte (non-glossy) and light red-colored fruits.

Plants of the new *Hypericum* can be compared to plants of the *Hypericum* 'Kolmred', disclosed in U.S. Plant Pat. No. 13,554. In side-by-side comparisons, conducted in Boskoop, The Netherlands, plants of the new *Hypericum* differed primarily from plants of 'Kolmred' in the following characteristics:

1. Plants of the new *Hypericum* and 'Kolmred' differed in leaf lower surface color as plants of 'Kolmred' had leaves with green-colored lower surfaces.
2. Plants of the new *Hypericum* and 'Kolmred' differed in fruit shape plants of 'Kolmred' had elliptic-shaped fruits.
3. Plants of the new *Hypericum* and 'Kolmred' differed in fruit luster as plants of 'Kolmred' had matte (non-glossy) fruits.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet comprises a side perspective view of a typical flowering plant of 'Kolmiglow' grown in a container.

The photograph on the second sheet is a close-up view of a typical stems and leaves of 'Kolmiglow'.

The photograph on the third sheet is a close-up view of a typical flower and developing flower buds of 'Kolmiglow'.

The photograph on the fourth sheet is a close-up view of a typical fruit of 'Kolmiglow'.

DETAILED BOTANICAL DESCRIPTION

Plants used for the aforementioned photographs and following description were grown in 22-cm containers during the autumn in an outdoor nursery in Boskoop, The Netherlands and under cultural practices typical of commercial *Hypericum* production. During the production of the plants, day temperatures ranged from 12° C. to 25° C. and night temperatures ranged from 4° C. to 15° C. Plants were three years old when the photographs and description were taken. In the following description, color references are made to The Royal Horticultural Society Colour Chart, 2007 Edition, except where general terms of ordinary dictionary significance are used.

Botanical classification: *Hypericum×inodorum* 'Kolmiglow'.

Parentage:

*Female, or seed, parent.*—Proprietary selection of *Hypericum×inodorum* identified as code number 8205-04, not patented.

*Male, or pollen, parent.*—Proprietary selection of *Hypericum×inodorum* identified as code number 393-00, not patented.

Propagation:

*Type cutting.*—Vegetative cuttings.

*Time to initiate roots, summer.*—About two weeks at temperatures about 20° C.

*Time to produce a rooted young plant, summer.*—About two months at temperatures ranging from 15° C. to 20° C.

*Root description.*—Fine, fibrous; white in color.

*Rooting habit.*—Moderately freely branching; medium density.

Plant description:

*Plant and growth habit.*—Perennial shrub; upright and outwardly spreading plant habit, broad inverted triangle; moderately vigorous growth habit.

*Branching habit.*—Freely basally branching habit with about 24 lateral branches developing per plant; pinching enhances lateral branch development.

*Plant height.*—About 39 cm.

*Plant width (spread).*—About 39.5 cm.

*Lateral branch description.*—Length: About 15.2 cm. Diameter: About 2.5 mm. Internode length: About 3.1 cm. Strength: Moderately strong to strong. Texture: Smooth, glabrous. Color, developing: Close to 187B. Color, fully developed: Close to N199C to N199D.

Leaf description:

*Arrangement.*—Opposite, simple; sessile.

*Length.*—About 5.1 cm.

*Width.*—About 3.2 cm.

*Shape.*—Ovate.

*Apex.*—Retuse.

*Base.*—Truncate to obtuse.

*Margin.*—Entire.

*Texture, upper and lower surfaces.*—Smooth to slightly rugose; glabrous.

*Venation pattern.*—Pinnate.

*Color.*—Developing leaves, upper surface: Close to 146A. Developing leaves, lower surface: Between 183A and 187B. Fully expanded leaves, upper surface: Close to 147A; towards the margins, close to 203B; venation and random sectors, close to 187A to 187B. Fully expanded leaves, lower surface: Close to 187B; venation, close to 185A.

Flower description:

*Flower type, arrangement and flowering habit.*—Single rotate flowers arranged in terminal and axillary compound cymes; freely flowering habit with about six flowers per cyme and about 280 flowers developing during the flowering season; flowers face mostly upright.

*Fragrance.*—None detected.

*Natural flowering season.*—Plants flower continuously from mid-June to mid-August in The Netherlands.

*Flower longevity.*—Flowers last about two or three days on the plant; flowers not persistent.

*Fruit longevity.*—About one month on the plant.

*Flower buds.*—Length: About 7 mm. Diameter: About 7 mm. Shape: Globular. Color: Close to 187B; towards the base, close to 185A and 53A.

*Inflorescence height.*—About 3.7 cm.

*Inflorescence diameter.*—About 4.4 cm.

*Flower diameter.*—About 2.3 cm.

*Flower depth (height).*—About 1.8 cm.

*Petals.*—Quantity and arrangement: Five in a single whorl. Length: About 1.1 cm. Width: About 9 mm. Shape: Obovate; concave; slightly reflexed. Apex: Bluntly acute. Base: Attenuate. Margin: Entire. Texture, upper and lower surfaces: Smooth, glabrous. Color: When opening and fully opened, upper surface: Close to 13A to 13B; color becoming closer to 16C with development. When opening and fully opened, lower surface: Close to 53A; towards the margins and base, close to 46B.

*Sepals.*—Quantity and arrangement: Five in a single whorl. Length: About 1.1 cm. Width: About 8 mm. Shape: Ovate to broadly ovate. Apex: Rounded. Base: Broadly cuneate. Margin: Entire. Texture, upper and lower surfaces: Smooth, glabrous. Color: When opening, upper surface: Close to 200A. When opening, lower surface: Close to 187A to 187B. Fully opened, upper surface: Close to 200A tinged with close to 147A. Fully opened, lower surface: Close to 187B.

*Peduncles.*—Length: About 2.1 cm. Diameter: About 1.5 mm. Texture: Smooth, glabrous. Strength: Moderately strong. Color: Close to 187A to 187B.

*Pedicels.*—Length: About 1 cm. Diameter: About 1 mm. Texture: Smooth, glabrous. Strength: Moderately strong. Color: Close to 187A.

*Reproductive organs.*—Stamens: Quantity per flower: About 75. Filament length: About 1 mm. Filament color: Close to 24B. Anther length: About 0.5 mm. Anther shape: Broadly oval. Anther color: Close to 13B to 13C. Pollen amount: Scarce. Pollen color: Yellowish. Pistils: Quantity per flower: Single pistil with three stigmas. Pistil length: About 3 mm. Stigma shape: Club-shaped. Stigma color: Close to N186A. Style length: About 2 mm. Style color: Close to 42B; towards the base, close to 154C. Ovary color: Close to 45A and 46B.

*Fruits.*—Length: About 1.1 cm. Diameter: About 9 mm. Shape: Ovate. Texture: Smooth, glabrous. Luster: Glossy. Color: Close to 53A; towards the apex, close to 187A.

*Seeds.*—Length: About 0.9 mm. Diameter: About 0.5 mm. Color: Close to 200A.

Disease & pest resistance: Plants of the new *Hypericum* have been noted to be resistant to *Puccinia* rust. Plants of the new *Hypericum* have not been observed to be resistant to pests and other pathogens common to *Hypericum* plants.

Weather & temperature tolerance: Plants of the new *Hypericum* have been observed to tolerate wind, rain and temperatures ranging from about −20° C. to about 40° C.

It is claimed:

1. A new and distinct *Hypericum* plant named 'Kolmiglow' as illustrated and described.

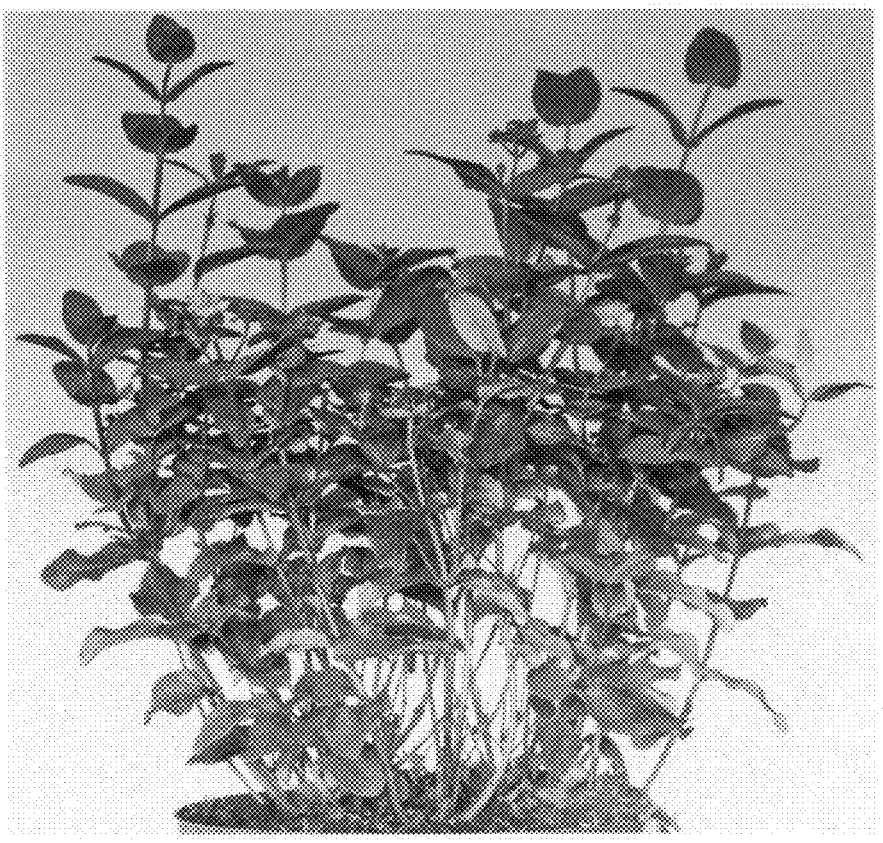

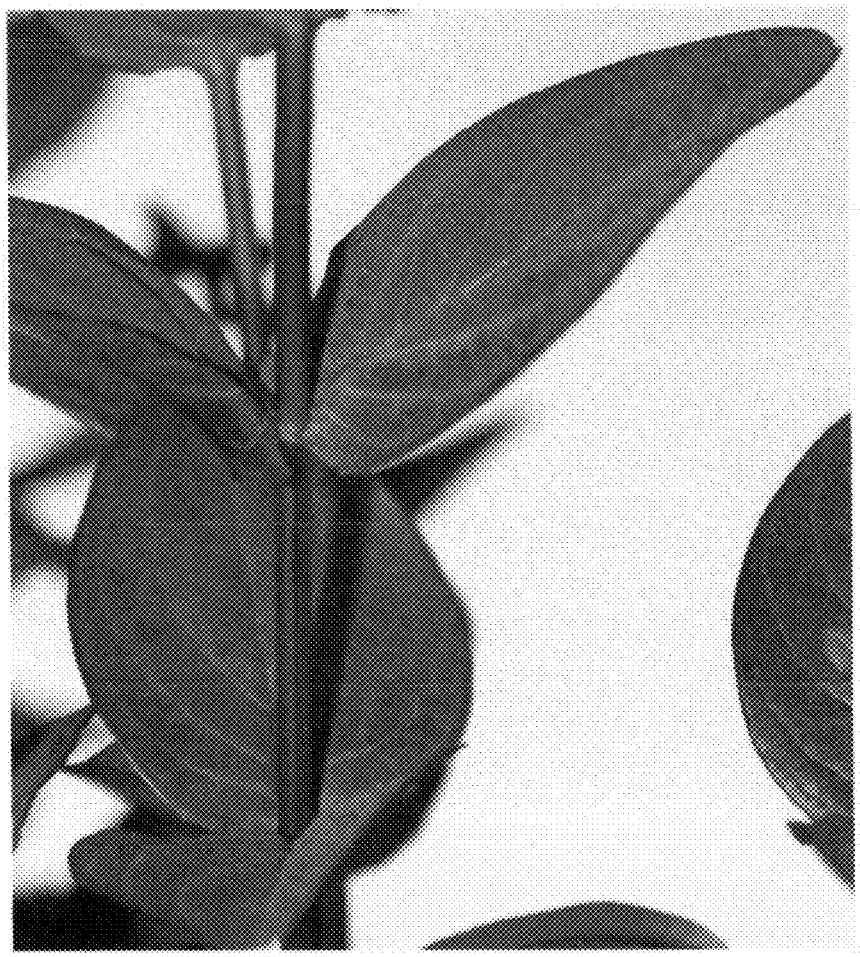

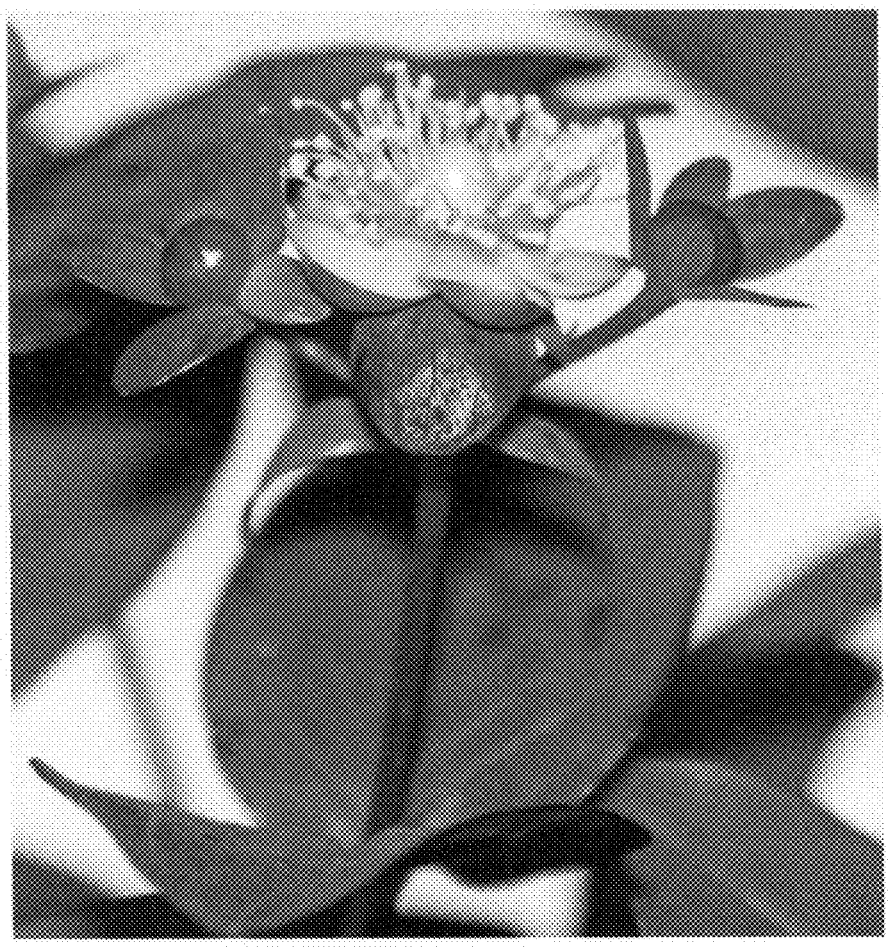

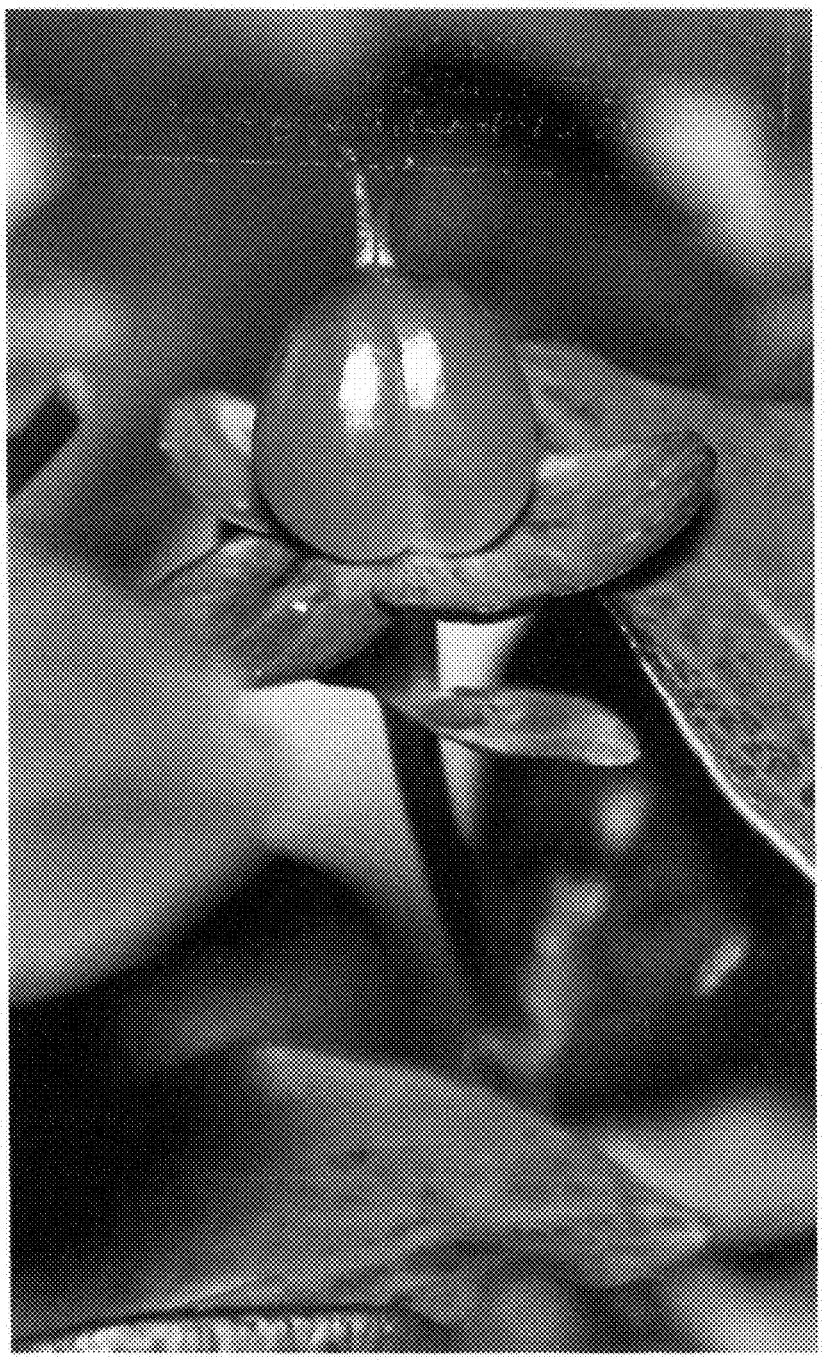

* * * * *